United States Patent
Pyles

(10) Patent No.: US 11,227,340 B2
(45) Date of Patent: *Jan. 18, 2022

(54) EXERCISE APPARATUS WITH EXERCISE USE VERIFICATION FUNCTION AND VERIFYING METHOD

(71) Applicant: JOHNSON HEALTH TECH CO., LTD, Taichung (TW)

(72) Inventor: Nathan Pyles, Lake Mills, WI (US)

(73) Assignee: JOHNSON HEALTH TECH CO., LTD, Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/327,418

(22) Filed: May 21, 2021

(65) Prior Publication Data

US 2021/0279813 A1 Sep. 9, 2021

Related U.S. Application Data

(63) Continuation of application No. 17/026,847, filed on Sep. 21, 2020, which is a continuation of application
(Continued)

(51) Int. Cl.
*G06Q 40/08* (2012.01)
*A63B 24/00* (2006.01)
(Continued)

(52) U.S. Cl.
CPC ......... *G06Q 40/08* (2013.01); *A63B 22/0235* (2013.01); *A63B 24/0062* (2013.01); *A63B 24/0087* (2013.01); *G16H 20/30* (2018.01); *A63B 22/025* (2015.10); *A63B 22/04* (2013.01); *A63B 2024/0093* (2013.01); *A63B 2024/0096* (2013.01); *A63B 2220/13* (2013.01); *A63B 2220/20* (2013.01); *A63B 2220/30* (2013.01);
(Continued)

(58) Field of Classification Search
CPC ................ G06Q 40/08; A63B 22/0235; A63B 24/0062; A63B 24/0087; A63B 22/025; A63B 22/04; A63B 2024/0093; A63B 2024/0096; A63B 2220/13; A63B 2220/20; A63B 2220/30; A63B 2220/56; A63B 2220/62; A63B 2220/805; A63B 2225/20; A63B 2225/50; A63B 2230/50; A63B 2230/505; G16H 20/30
See application file for complete search history.

(56) References Cited

U.S. PATENT DOCUMENTS

| | | |
|---|---|---|
| 6,575,878 B1 | 6/2003 | Choy |
| 6,638,198 B1 | 10/2003 | Shea |
| 8,007,408 B1 | 8/2011 | Moran et al. |
| 8,287,434 B2 | 10/2012 | Zavadsky et al. |

(Continued)

*Primary Examiner* — Sundhara M Ganesan
(74) *Attorney, Agent, or Firm* — Michael Best & Friedrich LLP

(57) ABSTRACT

An exercise apparatus includes a base, an operating unit that is movable relative to the base, and a motor that is coupled to the operating unit. The exercise apparatus also includes a sensor that is operable to detect engagement of a user with the operating unit, and a controller that is in communication with the operating unit and the sensor. The controller con generate validated exercise use data in response to the sensor detecting engagement of the user with the operating unit and movement of the operating unit relative to the base.

20 Claims, 6 Drawing Sheets

Related U.S. Application Data

No. 16/043,925, filed on Jul. 24, 2018, now Pat. No. 10,796,375, which is a continuation of application No. 14/983,171, filed on Dec. 29, 2015, now Pat. No. 10,032,227.

(60) Provisional application No. 62/098,309, filed on Dec. 30, 2014.

(51) Int. Cl.
  *G16H 20/30* (2018.01)
  *A63B 22/02* (2006.01)
  *A63B 22/04* (2006.01)

(52) U.S. Cl.
  CPC ....... *A63B 2220/56* (2013.01); *A63B 2220/62* (2013.01); *A63B 2220/805* (2013.01); *A63B 2225/20* (2013.01); *A63B 2225/50* (2013.01); *A63B 2230/50* (2013.01); *A63B 2230/505* (2013.01)

(56) References Cited

U.S. PATENT DOCUMENTS

| | | |
|---|---|---|
| 8,690,735 B2 | 4/2014 | Watterson et al. |
| 8,956,268 B2 | 2/2015 | Huang et al. |
| 9,039,580 B1 | 5/2015 | Bayerlein et al. |
| 2006/0205566 A1 | 9/2006 | Watterson et al. |
| 2009/0176629 A1 | 7/2009 | Yi |
| 2010/0016678 A1 | 1/2010 | Beck et al. |
| 2012/0040799 A1 | 2/2012 | Jaquish et al. |
| 2012/0296455 A1* | 11/2012 | Ohnemus ............... G16H 10/60 700/91 |
| 2013/0035215 A1 | 2/2013 | Ashby et al. |
| 2013/0143718 A1 | 6/2013 | Pani et al. |
| 2013/0211562 A1 | 8/2013 | Winter et al. |
| 2013/0274066 A1 | 10/2013 | Ashby et al. |
| 2013/0330694 A1* | 12/2013 | Watterson ............ A61B 5/0022 434/247 |
| 2014/0256512 A1* | 9/2014 | Kaiser ................ A63B 22/0694 482/9 |
| 2015/0066171 A1* | 3/2015 | Brussog ................ G16H 40/63 700/91 |
| 2015/0119202 A1 | 4/2015 | Hendrickson et al. |
| 2015/0238817 A1 | 8/2015 | Watterson et al. |

\* cited by examiner

EXERCISE APPARATUS WITH EXERCISE USE VERIFICATION FUNCTION AND VERIFYING METHOD

CROSS-REFERENCE TO RELATED APPLICATIONS

This application is a continuation of U.S. application Ser. No. 17/026,847, filed Sep. 21, 2020, which is a continuation of U.S. application Ser. No. 16/043,925, filed on Jul. 24, 2018, now U.S. Pat. No. 10,796,375, which is a continuation of U.S. application Ser. No. 14/983,171, filed on Dec. 29, 2015, now U.S. Pat. No. 10,032,227, which claims priority to U.S. Provisional Patent Application No. 62/098,309, filed Dec. 30, 2014, of which the entire contents of all are incorporated herein by reference.

BACKGROUND

The present disclosure relates to an exercise apparatus. More particularly, the present disclosure relates to an exercise apparatus with exercise use verification function and verifying method.

Some insurance companies often give their customers a choice of paying more or proving that they regularly exercise. Clearly, if the customers demonstrate measurable healthy habits, including proof of regular exercise, the insurance companies can often pay less money toward insurance payouts, and can then pass a portion of these savings onto their customers. Under this arrangement, the insurance companies would encourage their customers to regularly exercise and keep healthy. In this situation, the customers stay healthy, there are fewer expensive insurance payouts due to poor health, and it is more profitable for the insurance companies. In order to demonstrate beneficial exercise habits of an insurance customer to their insurance company, a conventional exercise apparatus with an exercise use data reporting function (such as the embodiments disclosed in U.S. Pat. Nos. 8,287,434 and 6,638,198) comes to the world.

U.S. Pat. Nos. 8,287,434 and 6,638,198 both disclose a conventional exercise apparatus that can provide exercise use data therefrom for a user. The exercise use data would represent an exercise amount of the user. The user could demonstrate his (or her) exercise habit and exercise use to their insurance company, via this data. The conventional exercise apparatus comprises an operating member and a controller associated with the operating member. When the user drives the operating member to operate the exercise apparatus, the controller associated with the operating member creates exercise use data. Thereafter, the controller records the exercise use data and reports the exercise use data to the user. The user could use this exercise use data to demonstrate his (or her) exercise habit. Provided with this exercise use data, the user's insurance company may then offer discounts to the user.

Currently, exercise use data is restricted to exercise apparatus with a user-driven operating member, which is driven by the user to operate the exercise apparatus. Examples of a user-driven operating member of an exercise apparatus would be a stationary bike operating member (a crank shaft, driven by the bike pedals) or an elliptical trainer operating member (a crank shaft, driven by the elliptical pedals and linkage system). Currently, if the controller is set to record exercise use data on an exercise apparatus with motor-driven operating member, such as a treadmill operating member (a motor driven running belt) or a stairclimber operating member (a motor driven staircase), it would be easy to falsify exercise use data on the exercise apparatus. The user could just turn on a motor-driven operating member of an exercise apparatus, without actually using the exercise apparatus, and let a controller associated with the operating member create exercise use data. A specific example would be a user turning on a motorized treadmill, causing the running belt to move, and letting the treadmill run until the treadmill controller had recorded a large distance traveled by the running belt. The user would not need to be present on the treadmill, and yet the treadmill controller would record exercise use data. As a result, the controller thereof would record the exercise use data which is faked. To avoid this, manufactures have, to date, reported only exercise use data associated with user-driven operating members to insurance companies, because the faked exercise use data shouldn't represent the exercise habit or amount of user exercise to the insurance companies. In other words, exercise apparatus with motor-driven operating members currently on the market wouldn't help the user to demonstrate his (or her) exercise habits to an insurance company. Therefore, if one buys an exercise apparatus with a motor-driven operating member, he (or she) couldn't demonstrate his (or her) exercise habits via the exercise apparatus, because there is a question as to the validity of this exercise use data.

SUMMARY

The present invention has arisen to mitigate and/or obviate the disadvantages of the conventional exercise apparatus. Further benefits and advantages of the present invention will become apparent after a careful reading of the detailed description with appropriate reference to the accompanying drawings.

The present invention involves an exercise apparatus with exercise use verification function and a verifying method. Generally speaking, the exercise apparatus with exercise use verification function is to verify an exercise use thereof, and the verifying method is to verify an exercise use of an exercise apparatus. Therefore, for example, a user could demonstrate his (or her) exercise habit to their insurance company.

The invention provides, in one aspect, an exercise apparatus that includes a base, an operating unit movable relative to the base, a motor coupled to the operating unit, a sensor operable to detect engagement of a user with the operating unit, and a controller in communication with the operating unit and the sensor. A communication interface is in communication with the controller, wherein the controller is configured to generate a non-validated exercise use data in response to movement of the operating unit relative to the base and the sensor does not detect engagement of the user with the operating unit, wherein the controller is further configured to generate a validated exercise use data in response to movement of the operating unit relative to the base and the sensor does detect engagement of the user with the operating unit, and wherein the controller transmits the validated exercise use data to the communication interface.

The invention provides, in another aspect, a method of verifying the use of an exercise apparatus that includes operating a motor-driven operating member, generating a non-validated exercise use data in response to operating the motor-driven operating member, detecting engagement of the motor-driven operating member by a user, recording the non-validated exercise use data as validated exercise use data for a portion of time in response to detecting engagement of the motor-driven operating member by the user, and reporting the validated exercise use data to a communication interface.

The invention provides, in yet another aspect, a motorized treadmill that includes a base, an endless belt movable relative to the base, a motor operably coupled to the endless belt, a sensor configured to detect engagement of the endless belt by a user, and a controller configured to record validated exercise use data in response to the sensor detecting of engagement of the endless belt by the user, the validated exercise data including an amount of user exercise time, the amount of user exercise time being generated by an amount of time that the sensor detects engagement of the endless belt by the user.

The invention provides, in yet another aspect, an exercise apparatus including a base, an operating unit that is movable relative to the base, and a motor that is coupled to the operating unit. The exercise apparatus also includes a sensor that is operable to detect engagement of a user with the operating unit, and a controller that is in communication with the operating unit and the sensor. The controller generates validated exercise use data in response to the sensor detecting engagement of the user with the operating unit and movement of the operating unit relative to the base.

The invention provides, in yet another aspect, an exercise apparatus including a motor, an operating member that is driven by the motor, and a sensor that is operable to detect engagement of a user with the operating member. The exercise apparatus also includes a controller that is in communication with the operating member and the sensor, and a communication interface in communication with the controller. The controller determines whether the user is engaged with the operating member in response to a signal from the sensor and movement of the operating member, and the controller reports exercise use data to the communication interface in response to the controller determining that the user is engaged with the operating member.

The invention provides, in yet another aspect, a method of verifying the use of an exercise apparatus. The method includes operating an operating member driven by a motor, generating exercise use data in response to operating the operating member, receiving, at a controller, sensor data from a sensor, comparing, at the controller, the sensor data with a known data parameter that is indicative of a user not engaging the operating member, and reporting, by the controller, the exercise use data to a communication interface in response to the comparison step indicating that the user is engaged with the operating member.

The reader is advised that this summary is not meant to be exhaustive. Further features, aspects, and advantages of the present invention will become better understood with reference to the following description, accompanying drawings and appended claims.

Further benefits and advantages of the present invention will become apparent after a careful reading of the detailed description with appropriate reference to the accompanying drawings.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

Figure 1:
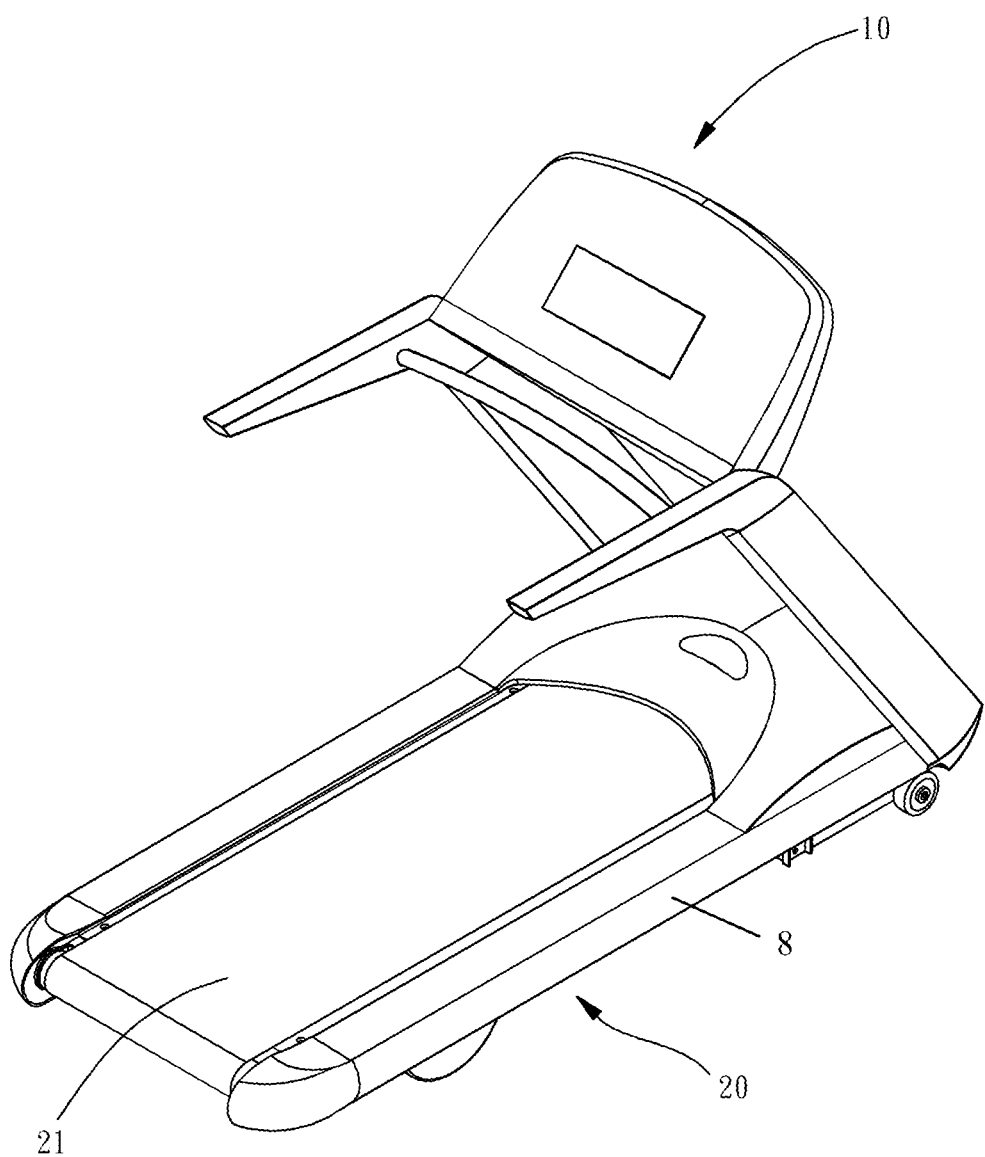
FIG. 1 is a perspective view of an exercise device embodying the present invention.
Figure 2:
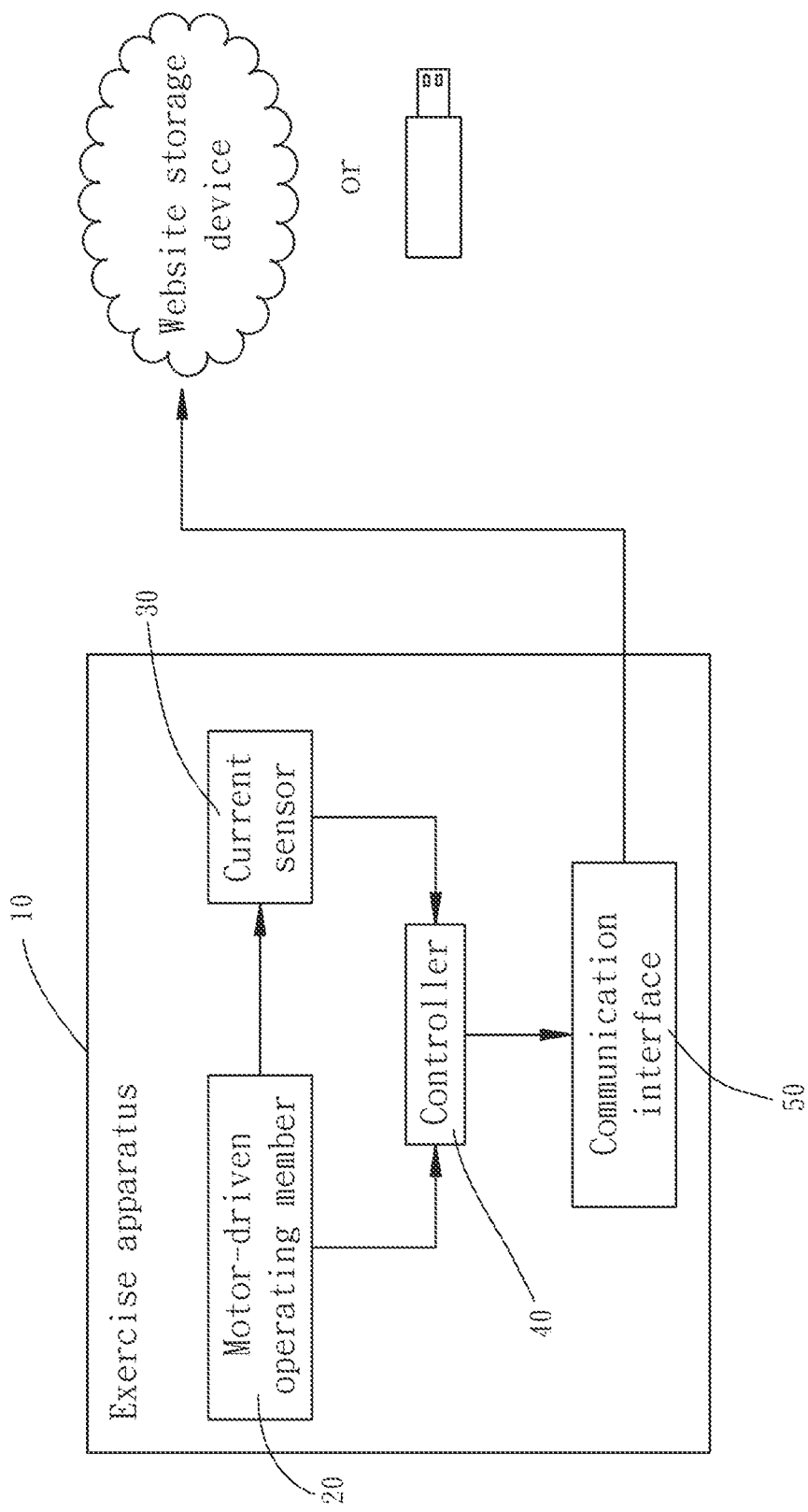
FIG. 2 is a schematic drawing of the exercise device and a data storage embodying the present invention.

FIGS. 1-2 illustrate an exercise apparatus 10 with an exercise use verification function. The exercise apparatus 10 comprises a base 8, a motor-driven operating member 20, a current sensor 30, a controller 40 associated with the motor-driven operating member 20 and the current sensor 30, and a communication interface 50 associated with the controller 40. Examples of an exercise apparatus can include a motorized treadmill (the embodiment of the present invention as shown in FIG. 1), a motorized stairclimber, or any other suitable types of motorized exercise equipment. In the embodiment illustrated in FIG. 1, the motor-driven operating member 20 includes an endless belt. It should be appreciated that the endless belt is provided for purposes of illustration, and the motor-driven operating member can be any suitable operating unit or operating member that a user of the exercise apparatus engages, contacts, or otherwise uses to perform the exercise. As an additional, non-limiting example of the motor-driven operating member, the exercise apparatus 10 can be a motorized stairclimber with the motor-driven operating member being a moving staircase.

Figure 3:
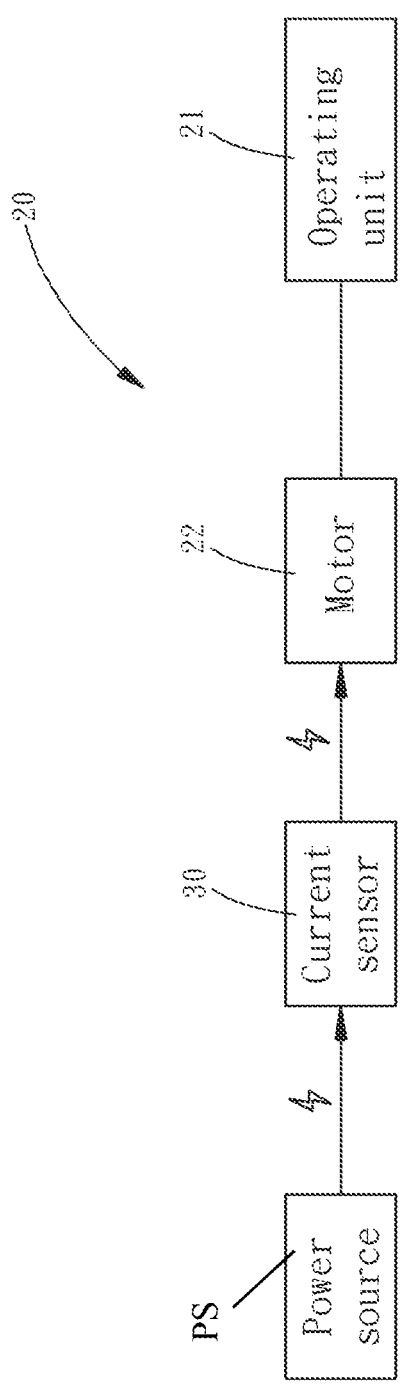
FIG. 3 is a schematic drawing of a motor-driven operating member and a power source embodying the present invention.

Referring to FIGS. 2-3, the motor-driven operating member 20 has an operating unit 21 (e.g., an endless belt, a staircase, etc.) and a motor 22. The motor 22 is structurally coupled to the operating unit 21 at one portion thereof. The motor 22 is electrically connected to a power source PS, such as an AC power socket, via a wire. The power source PS transmits an input current into the motor 22 via the wire so as to power the motor 22 to drive the operating unit 21. The current sensor 30 is associated with the motor 22 by being positioned between the motor 22 and the power source PS. The current sensor 30 is configured to detect the input current in the wire, and generate a current signal proportional to the input current (the detail of the current sensor, such as how to detect electrical current in a wire or generate a signal, is well-known and will not be further described here).

The controller 40 is operable to receive data according to operation of the motor-driven operating member 20, and further operable to process the data. In the illustrated embodiment, the controller 40 includes a microcontroller unit, at least one electronic circuit, and at least one circuit board. The microcontroller unit and the electronic circuit are assembled on the circuit board so as to define a controller assembly. In other embodiments, the controller 40 can be a computer processing system that includes a hardware assembly, a software assembly, and/or a firmware assembly. The hardware assembly of the controller 40 can include a processor that is in communication with a computer readable storage medium. The computer readable storage medium can be any suitable data storage device that can store data that can be thereafter accessed and read by the controller (or components thereof) or a separate computing system. Examples of computer readable storage medium can include, but is not limited to, read-only memory, CD-ROM, CD-R, CD-RW, DVD, DVD-RW, magnetic tapes, Universal Serial Bus (USB) flash drive, or any other optical or other suitable data storage device.

As illustrated in FIG. 2, the controller 40 is in communication with the motor-driven operating member 20 and the current sensor 30. In addition, the current sensor 30 is in communication with the motor-driven operating member 20. The controller 40 is in communication with the communication interface 50. The communication between components can be by any suitable wired connection (e.g., a bus wire, etc.), any suitable wireless connection (e.g., Bluetooth, Wi-Fi, etc.), or a combination of suitable wired and wireless connections. The communication interface 50 facilitates transmission or communication of exercise use data (validated and/or unvalidated) from the exercise apparatus 10 for distribution. The communication interface 50 is discussed in additional detail below.

In operation, the current signal is transmitted from the current sensor 30 to the controller 40. Consequently, the controller 40 can continue to monitor a state of the input current. Specifically, if a user gets on the operating unit 21 during operation of the motor-driven operating member 20 (e.g., the endless belt illustrated in FIG. 1), the motor 22 will draw more current because the operating unit 21 undertakes the user footfall and needs more driving power from the motor 22 to keep regularly operating. Therefore, the current sensor 30 will detect whether or not the user is engaging the motor-driven operating member 20 by detecting a current change of the input current that is caused by the user footfall. Thereafter, the current sensor 30 transmits the current signal proportional to the input current to the controller 40, so that the controller 40 can further determine, via the current signal, whether or not the user is engaging (or continues to engage, or ceases to engage) the motor-driven operating member 20.

Referring back to the first embodiment of FIGS. 1-3, if the operating unit 21 is driven by the motor 22, the controller 40 creates a non-validated exercise use data according to operation of the motor-driven operating member 20. Simultaneously, the current sensor 30 detects the input current in the wire to the motor 22 so as to detect whether or not a user is engaging the motor-driven operating member 20, and generates a current signal proportional to the input current. Then, the current signal is transmitted from the current sensor 30 to the controller 40. In order to determine whether or not a user is engaging the motor-driven operating member, the controller 40 analyzes fluctuations in the input current. Fluctuations occur when a user is using the exercise apparatus 10 due to the user's foot contacting the operating unit 21 and briefly causing a change in resistance to movement of the operating unit 21. This change in resistance is met by a change in input current to the motor 22. The controller 40 can be programmed to analyze the amplitude and frequency of any fluctuations in order to determine whether or not a user is using the exercise apparatus. Such an analysis can be tailored to distinguish user-induced fluctuations from fluctuations caused by other factors, such as belt or roller imbalance. The user-induced fluctuations sensed when a user is using the exercise apparatus 10 would not be sensed when a user is not using the exercise apparatus 10.

For example, the controller 40 can be programmed to detect that a user is engaging the operating member 20 if fluctuations of the input current are at least 5% and are at a frequency of between 80/minute and 250/minute. The parameters will vary depending on the exercise apparatus, and can be chosen to distinguish from normal fluctuations in the motor, transmission, and belt.

Figure 4:
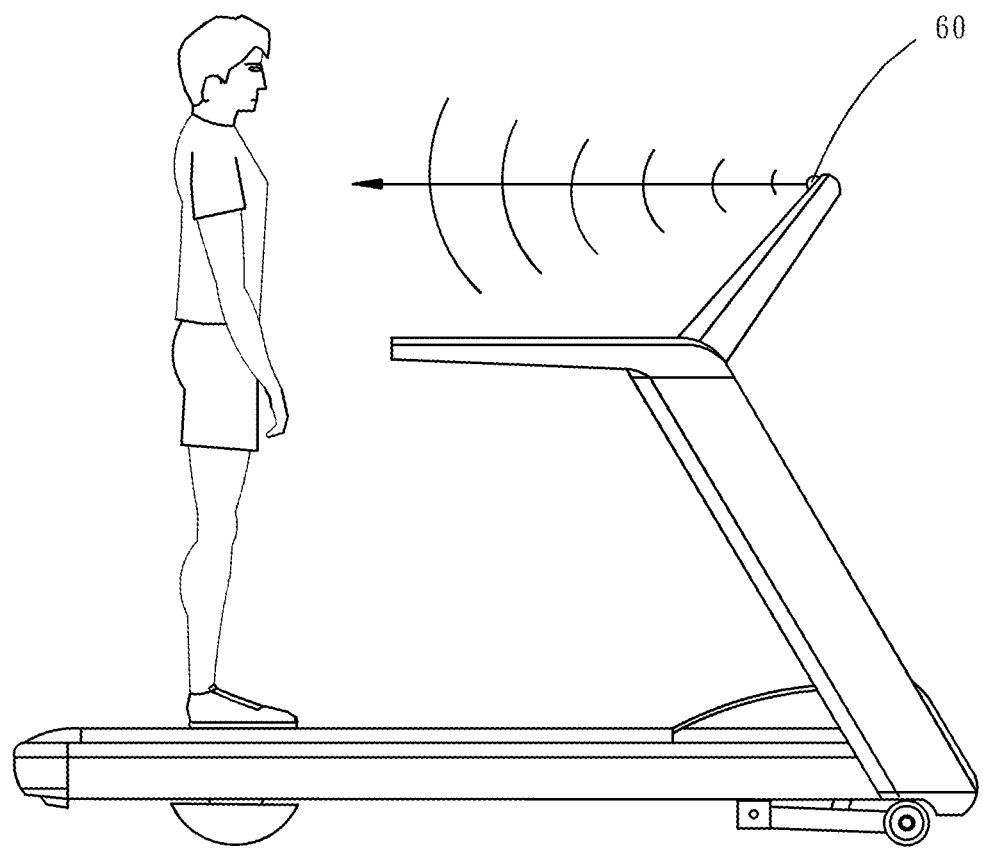
FIG. 4 is a side view of a second embodiment of the present invention.
Figure 5:
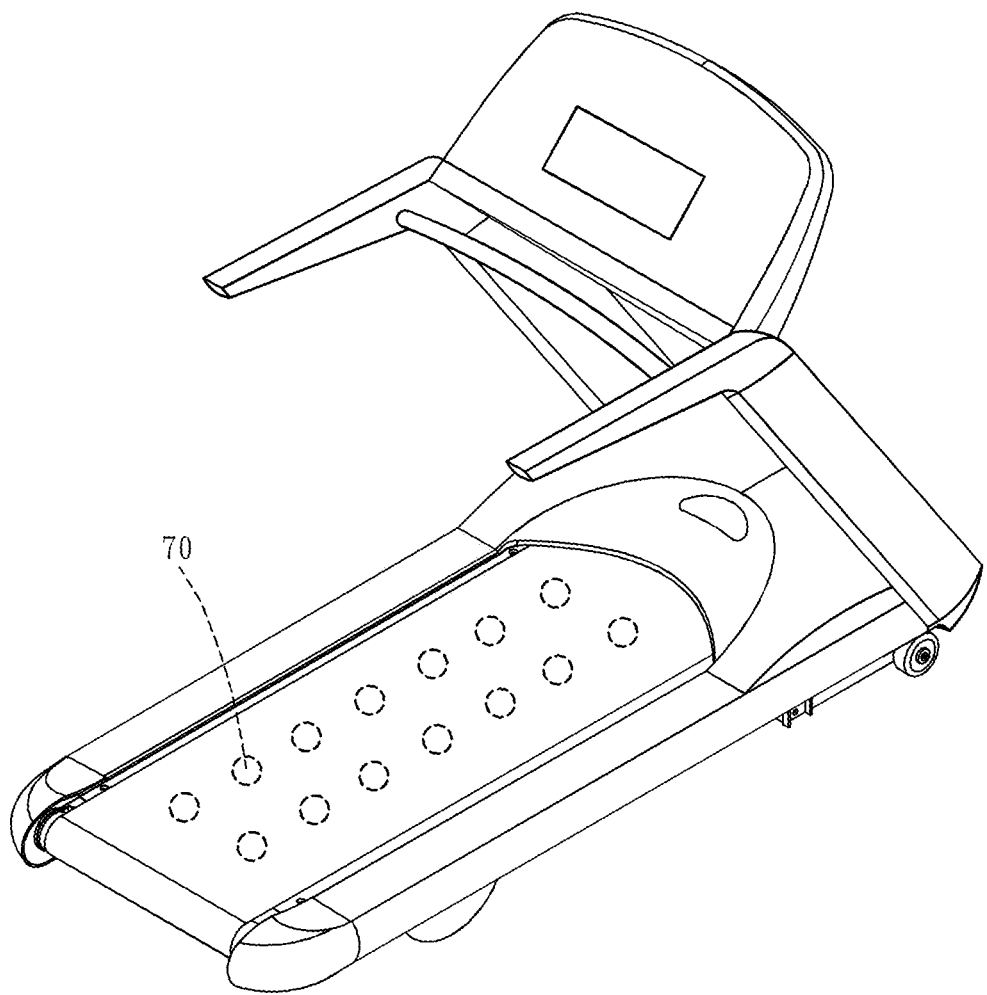
FIG. 5 is a perspective view of a third embodiment of the present invention.

Although a sensor that is configured to detect whether or not a user is engagement with the motor-driven operating member is illustrated in the embodiment of FIGS. 1-3 as the current sensor 30, in other embodiments other sensors can be implemented. For example, in other embodiments the sensor for detecting user engagement of the motor-driven operating member can be an optical sensor 60 that senses a level of IR radiation (see FIG. 4), a pressure sensor 70 that senses (or detect) an amount of pressure on the running belt (see FIG. 5), a speed sensor that senses fluctuations in speed of the operating unit, a thermal sensor that senses a level of heat (i.e., from a human body) on or near the motor-driven operating member, or any other suitable sensor. In each of these cases, the measured parameter can be compared to a default parameter that exists when a user is not engaging the motor-driven operating member. The detail of these sensing devices is well-known and will not be further described here.

If the user is not detected as engaging the motor-driven operating member 20, the controller 40 keeps creating non-validated exercise use data and monitoring the state of the input current in the wire to the motor 22. In contrast, if the user is detected as engaging the motor-driven operating member 20, the controller 40 records the non-validated exercise use data as validated exercise use data. Finally, the validated exercise use data is reported from the controller 40 to the communication interface 50. The validated exercise use data can further include an amount of time (or portion of time or accrued amount of time) the user is detected as engaging the motor-driven operating member 20 (i.e., the amount of time the user spends exercising), which can be based on a timer or other timing device that measures the amount of time the user is detected as engaging the motor-driven operating member 20. In addition, or alternatively, the validated exercise use data can include a distance traveled (or an equivalent distance traveled) by the user while the user is detected as engaging the motor-driven operating member 20 (i.e., the distance traveled by the user while exercising).

The communication interface 50 can communicate the exercise use data (e.g., validated and/or unvalidated exercise use data) to an interested third party (e.g., a physician, a medical provider, etc.), a demander (e.g., an insurance company, an insurance provider, etc.), and/or the user. For example, the communication interface 50 can be a display device, such as a screen of a console positioned on a portion of the exercise apparatus 10. The screen can be configured to display the validated exercise use data to the user. The user is then free to view and/or document (e.g., write down, etc.) the validated exercise use data so as to present it to the interested third party and/or demander. In this way, the validated exercise use data is substantially shown as a multimedia content, such as a media image and/or a sound. As another example, the communication interface 50 is configured to output the exercise use data to an outside storage device such as a flash drive, a disk rewriter, or a website storage device by a communication link. The communication link can be a port (or plug) that is configured to receive a computer readable storage medium (e.g., a USB flash drive, etc.). The validated exercise use data is substantially packaged in a computer file that can be accessed or processed to show the validated exercise use data as a multimedia content, such as the media image and/or the sound. Additionally or otherwise, the communication link can be a wired connection (e.g., a USB connection, a CAT-5 connection, etc.) or a wireless connection (e.g., an Internet interface, Wi-Fi, Bluetooth, etc.). In this way, the port (or plug) is replaced with (or can also further include) a wired and/or wireless communication module, and the outside storage device has a further corresponding wired and/or wireless communication module. The validated exercise use data can then be transmitted from the communication module of the exercise apparatus 10 to the communication module of the outside storage device (by the wired and/or wireless connection). In the illustrated embodiment shown in FIGS. 1-3, the communication interface 50 is illustrated as an Internet interface, such as a Wi-Fi internet module or an internet port. It should be appreciated that the outside storage device can be a web or Internet based storage device, such as a web based database. This allows for the communication of validated exercise use data to the interested third party or demander by via wireless internet connection or wired internet connection. Therefore, the user does not need to manually present the validated exercise use data to the interested third party or demander. In other examples of embodiments, the communication interface 50 can be programmed or incorporated into the controller 40 such that the controller 40 performs the functions associated with the communication interface 50 as described herein.

Figure 6:
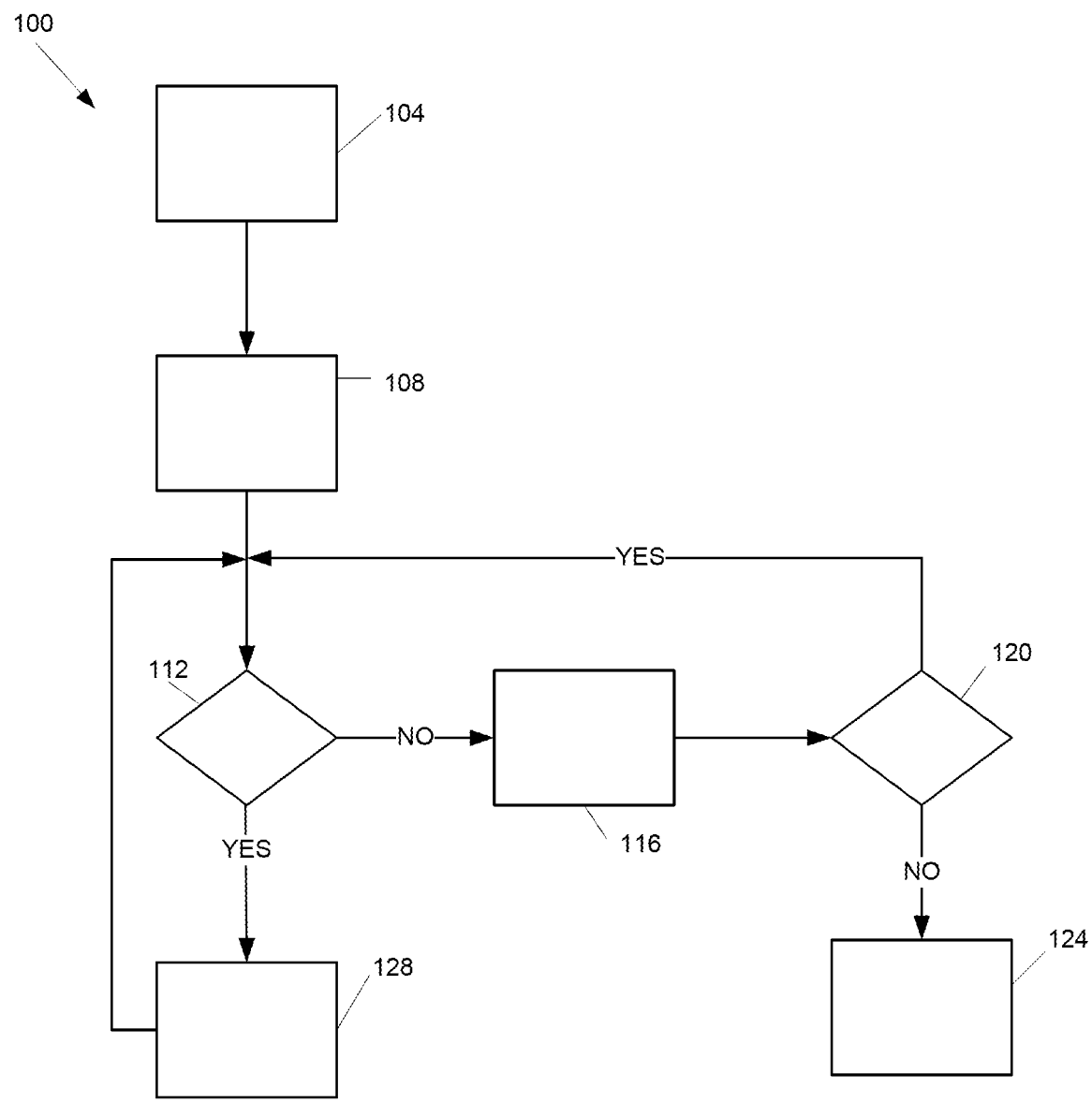
FIG. 6 is a flow diagram of an embodiment of an exercise use verification application that verifies use of the exercise device.

FIG. 6 illustrates an example of an exercise use verification application 100 that uses data acquired from the motor-driven operating member 20 to monitor and verify that a user is using the exercise equipment. The application 100 can be a module that operates on (or is associated with) the controller 40. The application 100 may be distributed and stored on the controller 40, and/or can be accessible from a remote location, such as through a web portal, web site, local area network, or generally over the Internet. The exercise use verification application 100 includes a series of processing instructions or steps that are depicted in flow diagram form.

Referring to FIG. 6, the process begins at step 104, where the exercise apparatus 10 is powered on and in an operational state. The application 100 is initiated, for example, by an interlock with the motor 22 such that when the motor 22 is in an operational state, the application 100 is also operational.

Next, at step 108 the controller 40 receives data from the sensor configured to detect user engagement with the exercise apparatus 10. For example, the controller 40 receives data from the current sensor 30. In other embodiments, the controller 40 receives data from the optical sensor 60, the pressure sensor 70, the speed sensor, the thermal sensor, or the other suitable sensor.

Proceeding to step 112, the controller 40 analyzes the data from the sensor to detect whether a user is actively engaging the motor-driven operating member 20. For example, the controller 40 can analyze fluctuations in the input current from the current sensor 30, as described above. In addition, or alternatively, the controller 40 can compare the received data from the sensor to a known (or default or standard) data parameter that is indicative of a user not engaging the motor-driven operating member 20. The known data parameter can be preprogrammed into the controller, or recognized during operational use (e.g., operation of the motor-driven operating member 20 without a user). If the analysis results in a "no," there is no user detected that is actively engaging the motor-driven operating member 20, the process proceeds to step 116. If the analysis results in a "yes," there is a user detected that is actively engaging the motor-driven operating member 20, the process proceeds to step 128, the details of which are later described.

At step 116, the process generates non-validated exercise use data. This data can be locally stored, or communicated to an interested third party, a demander, and/or the user as discussed above. Next, at step 120, the process detects whether the motor 22 (or motor-driven operating member 20) continues to operate. If the process detects that "yes" the motor 22 continues to operate, the process returns to step 112 and repeats. If the process detects that "no" the motor 22 does not continue to operate, which is indicative of the exercise apparatus 10 no longer operating, the process terminates at step 124.

At step 128, the process generates validated exercise use data. More specifically, the controller can record (or otherwise identify) the non-validated exercise use data as validated exercise use data. The validated exercise use data can be locally stored or communicated to an interested third party, a demander, and/or the user as discussed above. The process returns to step 112 and repeats.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

The invention claimed is:

1. An exercise apparatus comprising:
 a base;
 an operating unit movable relative to the base;
 a motor coupled to the operating unit;
 a sensor operable to detect engagement of a user with the operating unit;
 a controller in communication with the operating unit and the sensor, the controller configured to generate validated exercise use data in response to the sensor detecting engagement of the user with the operating unit and movement of the operating unit relative to the base.

2. The exercise apparatus of claim 1, wherein the controller is further configured to generate non-validated exercise use data in response to the sensor detecting the user not engaged with the operating unit and movement of the operating unit relative to the base.

3. The exercise apparatus of claim 2, wherein on startup of the motor and movement of the operating unit relative to the base, the controller is configured to generate the non-validated exercise use data, and wherein the controller is further configured to record the non-validated exercise use data as validated exercise use data in response to the sensor detecting engagement of the user with the operating unit.

4. The exercise apparatus of claim 1, wherein the validated exercise use data includes an amount of user exercise time defined by a duration that the sensor detects engagement of the user with the operating unit during movement of the operating unit relative to the base.

5. The exercise apparatus of claim 1, wherein the validated exercise use data includes a distance traveled by the user, wherein the distance traveled is defined while the sensor detects engagement of the user with the operating member.

6. The exercise apparatus of claim 1, wherein the controller is further configured to record the validated exercise use data in response to the sensor detecting engagement of the user with the operating unit.

7. The exercise apparatus of claim 1, wherein the controller is configured to establish communication with a remote location, and wherein the controller is configured to maintain communication between the exercise apparatus and the remote location while the user is determined by the controller not to be engaged with the operating member.

8. An exercise apparatus comprising:
a motor;
an operating member driven by the motor;
a sensor operable to detect engagement of a user with the operating member;
a controller in communication with the operating member and the sensor; and
a communication interface in communication with the controller,
wherein the controller is configured to determine whether the user is engaged with the operating member in response to a signal from the sensor and movement of the operating member,
wherein the controller is configured to report exercise use data to the communication interface in response to the controller determining that the user is engaged with the operating member.

9. The exercise apparatus of claim 8, wherein the controller is configured to stop reporting the exercise use data to the communication interface in response to the controller determining that the user is not engaged with the operating member and the operating member is driven by the motor.

10. The exercise apparatus of claim 8, wherein the controller is in communication with the communication interface while the operating member is driven by the motor and the user is determined by the controller not to be engaged with the operating member.

11. The exercise apparatus of claim 10, wherein the communication interface is in communication with a remote storage device while the operating member is driven by the motor and the user is determined by the controller not to be engaged with the operating member.

12. The exercise apparatus of claim 8, wherein the controller is configured to report the exercise use data to the communication interface only in response to the controller determining that the user is engaged with the operating member and the operating member is being driven by the motor.

13. A method of verifying the use of an exercise apparatus, the method comprising:

operating an operating member driven by a motor;
generating exercise use data in response to operating the operating member;
receiving, at a controller, sensor data from a sensor;
comparing, at the controller, the sensor data with a known data parameter that is indicative of a user not engaging the operating member; and
reporting, by the controller, the exercise use data to a communication interface in response to the comparison step indicating that the user is engaged with the operating member.

14. The method of claim 13, further comprising ceasing reporting of the exercise use data to the communication interface in response to the controller determining that the user is not engaged with the operating member while the operating member is driven by the motor.

15. The method of claim 13, further comprising generate the exercise use data in response to the determination that the user is engaged with the operating member and in response to the determination that the user is not engaged with the operating member while the operating member is being driven by the motor.

16. The method of claim 13, further comprising reporting, by the controller, the exercise use data to the communication interface only in response to the controller determining that the user is engaged with the operating member.

17. The method of claim 13, further comprising determining, by the controller, an amount of user exercise time defined by a duration that the sensor detects engagement of the user with the operating member during movement of the operating member.

18. The method of claim 13, wherein the known data parameter is recognized by the controller during operational use of the operating member.

19. The method of claim 13, wherein the reported exercise use data is defined as validated exercise use data.

20. The method of claim 13, further comprising connecting the exercise apparatus with a remote location, communicating the exercise use data to the remote location, and maintaining communication between the exercise apparatus and an remote location while the operating member is driven by the motor and the user is determined by the controller not to be engaged with the operating member.

* * * * *

(12) INTER PARTES REVIEW CERTIFICATE (3872nd)
United States Patent (10) Number: US 11,227,340 K1
Pyles (45) Certificate Issued: Feb. 10, 2025

(54) EXERCISE APPARATUS WITH EXERCISE USE VERIFICATION FUNCTION AND VERIFYING METHOD

(71) Applicant: Nathan Pyles

(72) Inventor: Nathan Pyles

(73) Assignee: JOHNSON HEALTH TECH CO., LTD

Trial Number:
IPR2023-01165 filed Aug. 2, 2023

Inter Partes Review Certificate for:
Patent No.: 11,227,340
Issued: Jan. 18, 2022
Appl. No.: 17/327,418
Filed: May 21, 2021

The results of IPR2023-01165 are reflected in this inter partes review certificate under 35 U.S.C. 318(b).

INTER PARTES REVIEW CERTIFICATE
U.S. Patent 11,227,340 K1
Trial No. IPR2023-01165
Certificate Issued Feb. 10, 2025

AS A RESULT OF THE INTER PARTES REVIEW PROCEEDING, IT HAS BEEN DETERMINED THAT:

Claims 1-20 are cancelled.

\* \* \* \* \*